JUNIPERUS CHINENSIS
Filed Oct. 1, 1969 2 Sheets-Sheet 1
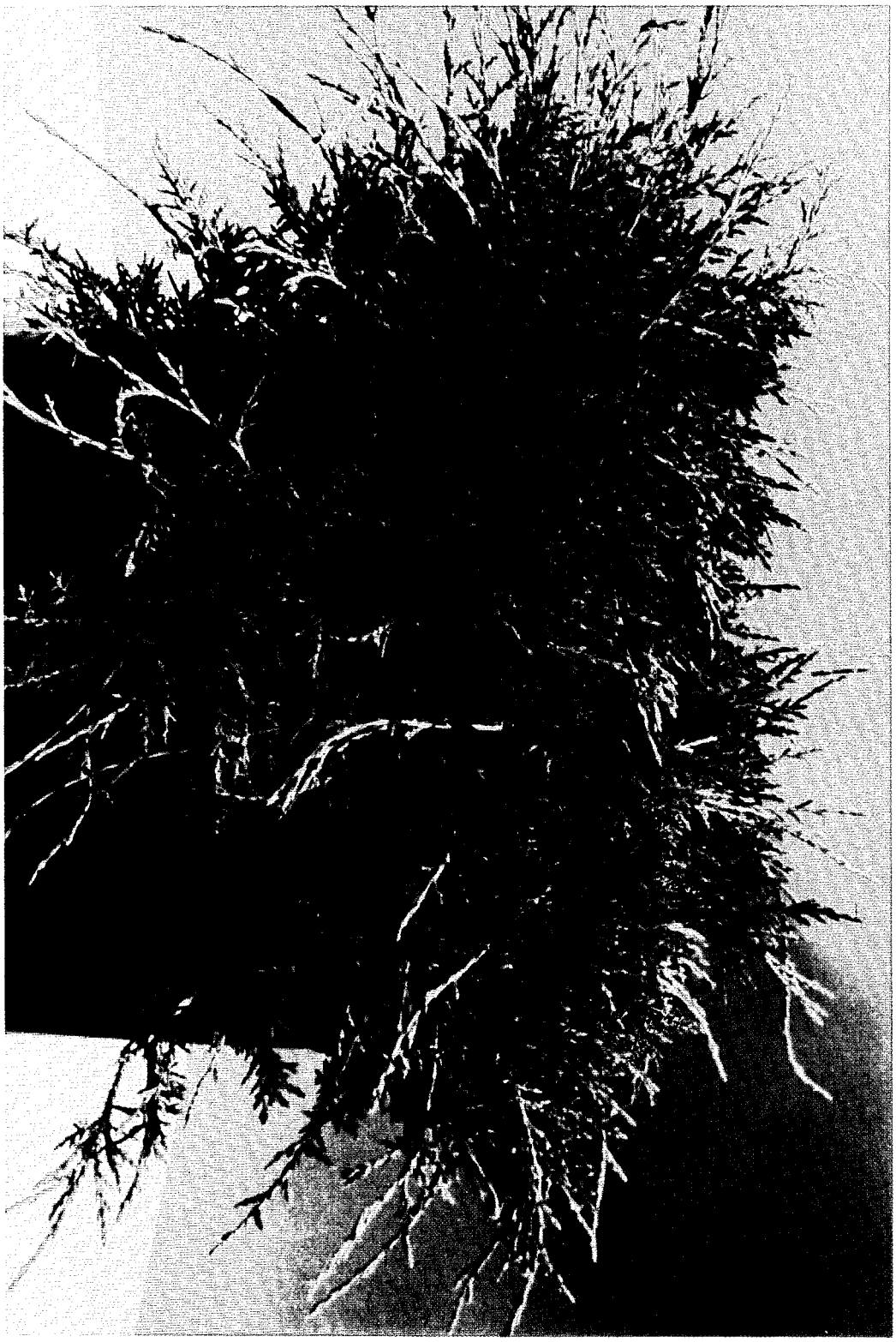

JUNIPERUS CHINENSIS
Filed Oct. 1, 1969 2 Sheets-Sheet 2
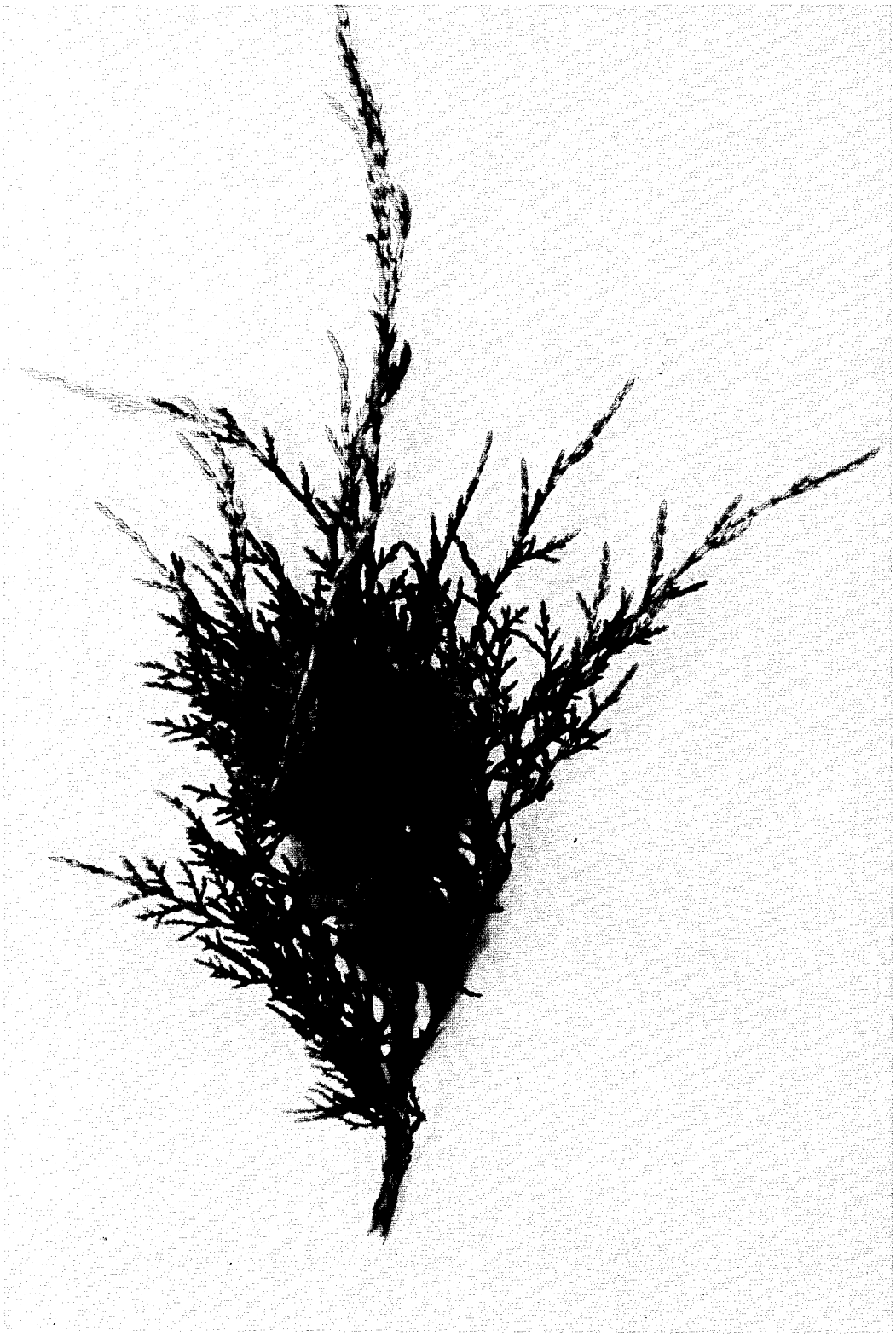

United States Patent Office

Plant Pat. 3,140
Patented Apr. 25, 1972

3,140
*JUNIPERUS CHINENSIS*

Frank J. Serpa, Fremont, Calif., assignor to Hines Wholesale Nurseries, Santa Ana, Calif.

Filed Oct. 1, 1969, Ser. No. 862,980
Int. Cl. A01h *7/00*
U.S. Cl. Plt.—50 1 Claim

The present invention relates to a new and distinct variety of *Juniperus chinensis* plant and more particularly to a plant of this genus (family Coniferae) which is an ornamental shrub.

I discovered this new variety on my cultivated property located at 40160 Mission Boulevard, in the City of Fremont, County of Alameda, State of California in June of 1963. The new variety originated as a sport of cultivated *Juniperus chinensis pfitzeriana glauca,* an unpatented variety.

My discovery of this sport was occasioned by the fact that while I was growing some 500 plants of *Juniperus chinensis pfitzeriana glauca,* this one plant appeared much different from all other plants in the block. I isolated the plant and made cuttings therefrom, and kept this plant and the cuttings under close observation. The outstanding characteristics of this plant were confirmed by these tests.

The new variety has been asexually reproduced by me on my cultivated property in Fremont, Calif. I additionally subjected a number of plants to tests elsewhere in Southern California. Several hundred cuttings of this new and distinct variety have been made since 1963, and in all instances the descendants have exhibited the distinguishing characteristics of the new variety, thereby establishing that the strain is true. The plant cannot be reproduced from seed.

Among the distinguishing characteristics and desirable factors in which this plant differs advantageously from its parent and any other juniper variety I know are these:

(1) Prostrate and compact habit of growth, requiring little or no trimming;

(2) An attractive brightness of color, which makes it an outstanding plant, whether grown singly or in groups;

(3) Slightly denser foliage than its parent;

(4) Entirely resistant to root problems, water-mold fungus or root-rot;

(5) Completely hardy to climatic conditions, having withstood temperatures ranging from 18° F. to 105° F. with no effect on the plant.

The accompanying drawings in color photographs show the entire plant and an enlarged view of one of the branches, and are as close to the natural colors as can be reproduced by this method of illustration.

To facilitate identification of the important colors, the color terminology adopted by the Horticultural Colour Chart of the British Colour Council has been employed.

*The plant*

Type: Evergreen shrub.

Parentage: Sport of *Juniperus chinensis pfitzeriana glauca,* an unpatented variety.

Growth habit: The shrub has compact and low growth habit.

Size: The shrub reaches a height of 6 to 8 inches above ground.

Approximate growth rate: In containers, growth varies from 9" to 15" annually. In large containers (15 gallon to 24" box) a spread of 6 feet has been reached in 4 to 5 years. Plants grown by the inventor in Fremont, Calif., and by the assignee on the Irvine Ranch, Orange County, in Southern California, have all been grown in containers. It is not known by either the inventor or the assignee what the lateral extent would be when planted in the ground and grown under excellent conditions of husbandry.

Blooms: None produced.

Foliage:

*Type.*—Needle-shaped and scale-like.

*Color.*—Upper side—Spinach Green, Plate 0960/2, page 187; underside—Lavender Green, Plate 000761/2, page 196; tips of new growth—Citron Green, Plate 763/2, page 100.

*Texture.*—Somewhat leathery, more leaflets than parent.

*Appearance.*—Compact.

*Disease and insect resistance.*—Compares very favorably with other junipers, as no water-mold fungus or root-rot has developed over several years of growth in Fremont, California. No insect problems have occurred requiring other than normal nursery spraying common to all nursery stock.

*Climatic range.*—Has withstood temperatures ranging from 18° F. to 105° F. without any harmful effect on the plant. While this specific plant has not been exposed to temperatures lower than 18° F., it derives from plants which are hardy in Zones 4 and 5, where low temperatures range from −30° F. to −10° F.

Comments of note: The plant maintains a compact, dense, and low shape, requiring little or no pruning. Freedom from diseases common to other junipers makes it a desirable plant in the garden. Of the thousands of plants grown in Fremont and on the Irvine Ranch, none have developed diseases common to other junipers.

Color: The branch color, in the Ameritone color key dictionary, is under color key #2, between 247C and 247D. The branch tip color, in the British Horticulture Chart, is under fern green, between 0862, line 2, and 0862 line 1, page 186.

Since the extremes of temperature in Central and Southern California are not very extensive, no significant color changes have been noted during the winter months. It should be noted that temperatures in Southern California have ranged from a low of 22° F. in December 1970 to 90° F. in January 1971. Possible color changes in other areas are not known to the inventor or the assignee.

Having described my invention, I claim:

1. A new and distinct variety of *Juniperus chinensis,* substantially as herein shown and described, characterized particularly as to novelty by its distinctive and unique compact and symmetrical low habit of growth, its restrained spreading habit, which makes pruning or trimming unnecessary, its relatively dense and profuse scale-like and needle-like foliage, its attractive color, its disease and pest resistance, and good temperature tolerance.

No references cited.

ROBERT E. BAGWILL, Primary Examiner